US012178852B2

(12) United States Patent
Kiani et al.

(10) Patent No.: US 12,178,852 B2
(45) Date of Patent: Dec. 31, 2024

(54) INSULIN FORMULATIONS AND USES IN INFUSION DEVICES

(71) Applicant: Willow Laboratories, Inc., Irvine, CA (US)

(72) Inventors: Massi Joe E. Kiani, Laguna Niguel, CA (US); Kevin Hughes Pauley, Lake Forest, CA (US); Venkatramanan Krishnamani, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 199 days.

(21) Appl. No.: 17/487,601

(22) Filed: Sep. 28, 2021

(65) Prior Publication Data

US 2022/0096603 A1    Mar. 31, 2022

Related U.S. Application Data

(60) Provisional application No. 63/085,344, filed on Sep. 30, 2020, provisional application No. 63/136,053, filed on Jan. 11, 2021.

(51) Int. Cl.
| | | |
|---|---|---|
| *A61K 38/28* | (2006.01) | |
| *A61K 9/00* | (2006.01) | |
| *A61K 45/06* | (2006.01) | |
| *A61K 47/42* | (2017.01) | |

(52) U.S. Cl.
CPC ............ *A61K 38/28* (2013.01); *A61K 9/0019* (2013.01); *A61K 45/06* (2013.01); *A61K 47/42* (2013.01)

(58) Field of Classification Search
None
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |

(Continued)

FOREIGN PATENT DOCUMENTS

| | | |
|---|---|---|
| AU | 2013201842 | 4/2013 |
| WO | WO 2012/174480 | 12/2012 |

(Continued)

OTHER PUBLICATIONS

US 2024/0016391 A1, 01/2024, Lapotko et al. (withdrawn)
Giger et al. "Suppression of Insulin Aggregation by Heparin" Biomacromolecules 9:2338-2344. (Year: 2008).*
Wilson et al. "Dual-Hormone Closed-Loop System Using a Liquid Stable Glucagon Formulation Versus Insulin-Only Closed-Loop System Compared with a Predictive Low Glucose Suspend System: An Open-Label, Outpatient, Single-Center, Crossover, Randomized Controlled Trial" Diabetes Care 43:2721-2729. (Year: 2020).*

(Continued)

*Primary Examiner* — Sudhakar Katakam
*Assistant Examiner* — Zachary J Miknis
(74) *Attorney, Agent, or Firm* — Knobbe, Martens, Olson & Bear, LLP

(57) ABSTRACT

Embodiments of the present disclosure provide insulin formulations having a near neutral pH and improved pharmacokinetic/pharmacodynamic properties, and uses in insulin infusion devices that may provide extended infusion period up to 7-14 days. Also provided are systems for administering insulin, the system may include a first reservoir, a second reservoir, an insulin pump configured to administer contents of the first reservoir or the second reservoir, and one or more hardware processors in communication with the insulin pump.

13 Claims, 5 Drawing Sheets

(56) References Cited

U.S. PATENT DOCUMENTS

| | | |
|---|---|---|
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |

(56) References Cited

U.S. PATENT DOCUMENTS

| | | |
|---|---|---|
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,244 B2 | 5/2016 | Li et al. |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| 9,993,529 B2 | 6/2018 | Yang et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,363,342 B2 * | 7/2019 | Dillon .................... A61L 29/06 |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |

(56) References Cited

U.S. PATENT DOCUMENTS

| | | |
|---|---|---|
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |

(56) References Cited

U.S. PATENT DOCUMENTS

| | | |
|---|---|---|
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0022592 A1 | 1/2013 | Vaughn et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0135682 A1 | 5/2014 | Frost et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0136097 A1 | 5/2017 | Soula et al. |
| 2017/0173632 A1 | 6/2017 | Al-Ali |
| 2017/0251974 A1 | 9/2017 | Shreim et al. |
| 2017/0290796 A1 | 10/2017 | Maneval et al. |
| 2017/0311891 A1 | 11/2017 | Kiani et al. |
| 2018/0236080 A1 | 8/2018 | Soula |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0310823 A1 | 11/2018 | Al-Ali et al. |
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0061706 A1 * | 3/2022 | Zade ............... A61K 38/28 |
| 2022/0071562 A1 | 3/2022 | Kiani |
| 2022/0096603 A1 | 3/2022 | Kianl et al. |
| 2022/0151521 A1 * | 5/2022 | Krishnamani ......... G16H 20/17 |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Klani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |

FOREIGN PATENT DOCUMENTS

| | | | |
|---|---|---|---|
| WO | WO-2012174480 A2 * | 12/2012 | ............. A61K 38/16 |
| WO | WO 2013/064787 | 5/2013 | |
| WO | WO 2013/177565 | 11/2013 | |
| WO | WO 2014/169081 | 10/2014 | |

(56) References Cited

FOREIGN PATENT DOCUMENTS

| WO | WO-2014169081 A2 * | 10/2014 | ............ A61J 1/1406 |
| WO | WO 2022/072383 | 4/2022 | |

OTHER PUBLICATIONS

International Search Report and Written Opinion received in PCT Application No. PCT/US2021/052474. dated Feb. 18, 2022 in 14 pages.

International Preliminary Report on Patentability and Written Opinion received in PCT Application No. PCT/US2021/052474. dated Apr. 13, 2023 in 10 pages.

* cited by examiner

INSULIN FORMULATIONS AND USES IN INFUSION DEVICES

INCORPORATION BY REFERENCE TO ANY PRIORITY APPLICATIONS

The present disclosure claims the benefit of priority to U.S. Ser. No. 63/085,344, filed Sep. 30, 2020 and U.S. Ser. No. 63/136,053, filed Jan. 11, 2021, each of which is hereby incorporated by reference in its entirety.

FIELD OF THE DISCLOSURE

The general field of this disclosure is insulin formulations and uses in infusion systems.

BACKGROUND

Diabetes is a chronic disease that impacts many individuals, both adults and children. The management of diabetes may include the measurement of glucose within the interstitial space including blood and/or interstitial fluid of a patient and administration of insulin to the patient. A closed loop insulin administration system often includes both a sensor to take glucose measurements from the interstitial space including blood and/or interstitial fluid of the patient, and an insulin administration device (e.g., an insulin infusion device) which administers insulin to the patient based on the glucose measurements. Closed loop insulin administration systems allow individuals impacted by diabetes to go about daily life with much less worry about their insulin or glucose levels which can vastly improve a diabetic's quality of life.

Insulin infusion devices face many challenges. They may not work properly or have undesirable side effects due to many reasons, including: catheter failure (45%), infusion site pain (20%), pull out (20%), adhesive failure (9%), or infection (6%). Many factors may cause catheter failure, for example, kinking of the catheter may be present in about 20% cases, and the reduced insulin action encapsulation, local thrombus or inflammation may be present in the remaining 80% cases. About 36% of insulin infusion failure is of biochemical nature. See Patel et al., Diabetes Technol Ther. 2014; 16(1): 15-19. As such, there remains a need to develop insulin formulations or coformulations with improved biochemical properties to reduce insulin infusion failures and provide desirable pharmacokinetic and pharmacodynamic properties for prolonged use of the insulin administration system.

SUMMARY

Some aspects of present disclosure relate to an insulin formulation, comprising: an effective amount of insulin and one or more insulin adjunctive excipients, wherein the insulin has a pH between about 6.8 and about 7.4. In some embodiments, the insulin adjunctive excipients comprise at least one hyaluronidase. In some embodiments, the insulin adjunctive excipients further comprise one or more insulin dissolution agents. In some embodiments, the insulin adjunctive excipients further comprise anti-platelet agents, anti-thrombosis agents, cell self markers, glucagon, glucagon activating agents, insulin inhibiting agents, or combinations thereof.

Some aspects of the present disclosure relate to a device for administering insulin formulation described herein. In particular, a device for administering insulin comprises: a first reservoir comprising an effective amount of insulin, wherein the insulin has a pH between about 6.8 and about 7.4; and a second reservoir comprising one or more insulin adjunctive excipients, wherein the insulin adjunctive excipients comprise at least one hyaluronidase. In some embodiments, the insulin adjunctive excipients in the second reservoir may further comprise insulin dissolution agents, anti-platelet agents, anti-thrombosis agents, cell self markers, glucagon, glucagon activating agents, insulin inhibiting agents, or combination thereof. In some embodiments, the content in in each of the first reservoir and the second reservoir may be administered separately and independently. In other embodiments, the content in each of the first reservoir and the second reservoir may be administered simultaneously or sequentially. In some embodiments, the insulin administering device described herein may provide an infusion of insulin for up to 7 days or 14 days.

Additional aspects of the present disclosure relate to a system for administering insulin. In some configurations, the system comprising: a device for administering insulin as described herein; an insulin pump configured to administer contents from the device to a subject; and one or more hardware processors in communication with the insulin pump. In some configurations, the one or more hardware processors configured to: determine a desired insulin response speed; determine, based on the desired insulin response speed, an infusion or insulin alone or an infusion of a combination of insulin and one or more insulin adjunctive excipients; and administer, using the insulin pump, the determined combination. In some embodiments, the insulin adjunctive excipients comprise one or more hyaluronidases, insulin dissolution agents, anti-platelet agents, anti-thrombosis agents, cell self markers, glucagon, glucagon activating agents, insulin inhibiting agents, or combination thereof.

DETAILED DESCRIPTION

Figure 1A:
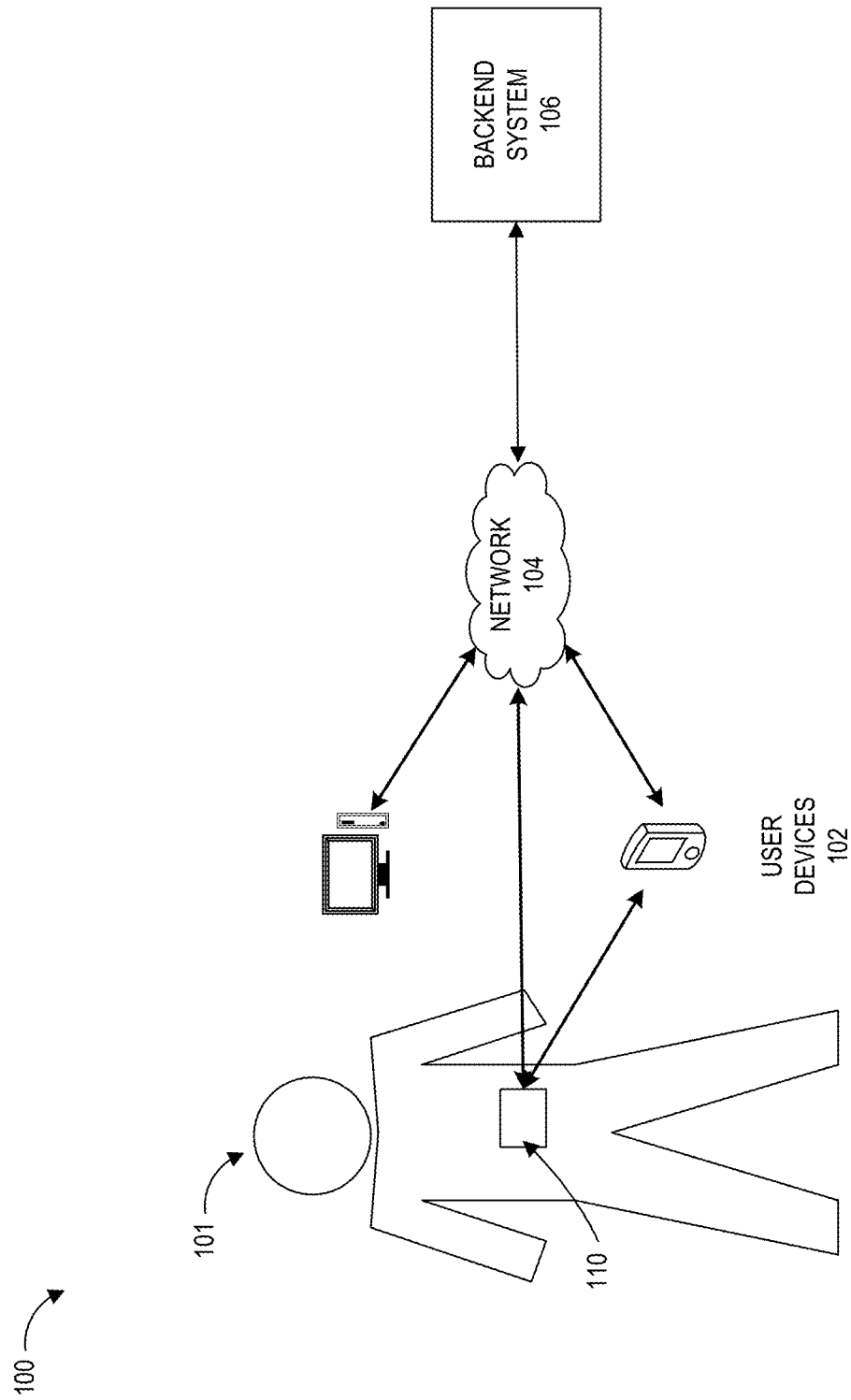
FIGS. 1A-1C illustrates an exemplary control system that may be used to administer insulin or one or more hyaluronidases.

Aspects of the disclosure will now be set forth in detail with respect to the figures and various examples. One of skill in the art will appreciate, however, that other configurations of the devices and methods disclosed herein will still fall within the scope of this disclosure even if not described in the same detail. Aspects of various configurations discussed do not limit the scope of the disclosure herein, which is instead defined by the claims following this description.

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. The terms "comprising," "including," "having," and the like are synonymous and are used inclusively, in an open-ended fashion, and do not exclude additional elements, features, acts, operations, and so forth.

That is, the above terms are to be interpreted synonymously with the phrases "having at least" or "including at least." For example, when used in the context of a process, the term "comprising" means that the process includes at least the recited steps, but may include additional steps. When used in the context of a device, the term "comprising" means that the device includes at least the recited features or components, but may also include additional features or components. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The term "and/or" as used herein has its broadest least limiting meaning, which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

Any methods disclosed herein need not be performed in the order recited. The methods disclosed herein include certain actions taken by a practitioner; however, they can also include any third-party instruction of those actions, either expressly or by implication.

Insulin Formulations

The present disclosure relates to insulin formulations for use in an insulin infusion device with improved pharmacokinetic (PK) and pharmacodynamic (PD) properties. The insulin formulation may provide fast acting insulin (for example, with a peak time of less than 15 minutes) with improved solubility and stability. In addition, the insulin formulations may improve solubility or provide less irritation to patient skin, and reduces the required hyaluronidase loading, thereby allowing for a high concentration of insulin formulation which can provide an extended infusion period.

Some aspects of the present disclosure relate to an insulin formulation comprising: an effective amount of insulin and one or more insulin adjunctive excipients, wherein the insulin has a pH between about 6.8 and about 7.4. In some further embodiments, the insulin formulation described herein has a pH of about 6.8, 6.9, 7.0, 7.1, 7.2, 7.3, or 7.4, or a range defined by any of the two preceding values. In one embodiment, the insulin formulation has a pH of about 7.0.

Hyaluronidases

In some embodiments of the insulin formulation described herein, the insulin adjunctive excipients comprise at least one hyaluronidase. Hyaluronidases are a family of hyaluronan-degrading enzymes. Hyaluronidases improves consistency and PK/PD of insulin dispersion in the dermis by eating away hyaluronic acid (also known as hyaluron or hyaluronan, the extracellular matrix or fibrinogen build up because of the scar tissue response). By removing hyaluronic acid or fibrinogen build up, the diffusion of insulin moves more freely and thus it improves the length of infusion time and the remaining usable the site of administration. Non-limiting examples of hyaluronidases to be used in insulin therapy has been reported by Halozyme Therapeutics Inc., for example, in U.S. Pat. Nos. 9,333,244 and 9,993,529 and U.S. Publications Nos. 2014/0135682, 2017/0290796, and 2013/0022592, each of which is incorporated by reference in its entirety. In some embodiments, the amount of the hyaluronidase(s) in the insulin formulation provided herein is between or about between 10 U/mL to 5000 U/mL, 50 U/mL to 4000 U/mL, 100 U/mL to 2000 U/mL, 300 U/mL to 2000 U/mL, 600 U/mL to 2000 U/mL, or 100 U/mL to 1000 U/mL. For example, the amount of one or more hyaluronidases is at least or is about or is 30 U/mL, 35 U/mL, 40 U/mL, 50 U/mL, 100 U/mL, 150 U/mL, 200 U/mL, 250 U/mL, 300 U/mL, 350 U/mL, 400 U/mL, 450 U/mL, 500 U/mL, 600 U/mL, 700 U/mL, 800 U/mL, 900 U/mL, 1000 U/mL or 2000 U/mL. In some embodiments, at least one hyaluronidase is in a lyophilized form.

Insulin Dissolution Agents

In some embodiments of the insulin formulation described herein, the insulin adjunctive excipients further comprise one or more insulin dissolution agents. In some cases, fast acting insulins form hexamers at a concentration of 100 IU/mL to ensure the stability of insulin in the commercial product while promoting the very rapid dissociation of these hexamers into monomers after injection subcutaneous to obtain rapid action. Human insulin, when in the form of monomers, it has a very strong propensity to aggregate and may lose activity and may also presents an immunological risk for the patient. The use of one or more insulin dissolution agents may facilitate the fast dissolution insulin hexamers into the active monomeric form. In some such embodiments, the insulin dissolution agents comprise citric acid, a salt, or a substituted derivative thereof. In some embodiments, the insulin in the formulation is in a hexameric form and the use of one or more insulin dissolution agents facilitates or improves the dispersion of insulin from hexameric to monomeric form. In some such embodiment, the insulin dissolution agents comprise sodium citrate. In some such embodiment, the insulin dissolution agents comprise a substituted citric acid derivative of the following structure:

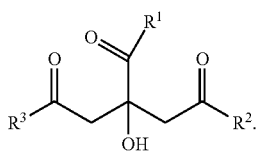

wherein each of $R^1$, $R^2$ and $R^3$ is independently OH or AA, at least one of the $R^1$, $R^2$ and $R^3$ is an AA radical, AA is a radical resulting from a natural or synthetic aromatic amino acid comprising at least one phenyl group or indole group, substituted or not substituted, said AA radical having at least one free carboxylic acid function, and the carboxylic acid functions are in the form of a salt of an alkali metal selected from Na+ and K+. Additional substituted citric acid derivative may include but not limited to

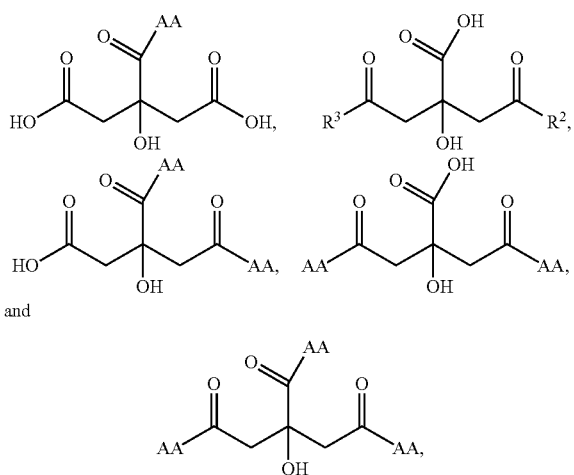

and all of which are disclosed in U.S. Publication No. 2017/0136097, which is incorporated by reference in its entirety. In some embodiments, the insulin dissolution agents may comprise one or more oligosaccharides. In further embodiments, the oligosaccharides have an average degree of polymerization between 3 and 13 and the polydispersity index greater than 1.0. In some further embodiments, the oligosaccharides have partially substituted carboxyl groups, wherein the unsubstituted carboxyl functional groups are salifiable. In further embodiments, the oligosaccharide is a dextran. Additional disclosure of the oligosaccharides used as insulin dissolution agent may be found in WO 2013/064787, which is incorporated by reference in its entirety.

In some embodiments of the insulin formulation described herein, the insulin adjunctive excipients further comprise one or more anti-platelet agents. In some such embodiments, the anti-platelet agents comprise nitric oxide (NO). In some instances, NO is generated or generatable from one or more nitric oxide donor compounds. Non-limiting examples of oxide donor compounds include S-nitroso-N-acetylpenicillamine (SNAP), N-diazeniumdiolate, S-nitrosothiols, metal nitrosyls, organic nitrates, and N-diazeniumdiolates, and combinations thereof. Chemicals like SNAP (S-nitroso-N-acetylpenicillamine) can slowly release NO to prevent thrombosis and infection. In some embodiments, the NO donor is a N-diazeniumdiolate (i.e., a 1-amino-substituted deazen-l-lum-1,2-diolate). N-Diazeniumdiolates are particularly attractive as NO donors due to their ability to generate NO spontaneously under biological conditions. In the formation of the N-diazeniumdiolate, one equivalent of amine reacts with two equivalents of nitric oxide under elevated pressure. A base (e.g., an alkoxide like methoxide) removes a proton from the amine nitrogen to create the anionic, stabilized [N(O)NO] group. While stable under ambient conditions, N-diazeniumdiolates decompose spontaneously in aqueous media to generate NO at rates dependent upon pH, temperature, and/or the structure of the amine moiety. For example, N-diazeniumdiolate-modified proline (PROLI/NO), 2-(dimethylamino)-ethylputreamlne (DMAEP/NO), N,N-dimethylhexanediamine (DMHD/NO), and diethylenetriamine (DETA/NO) have been developed as small molecule NO donors with diverse NO release half-lives ranging from 2 seconds to 20 hours at pH 7.4 and 37° C. Low molecular weight N-diazeniumdiolates NO donors, are among the most widely employed NO release compounds due to straightforward preparation, long-term stability if appropriately packaged/stored, and spontaneous degradation to NO into solution in physiological media.

Anti-Thrombosis Agents/Anticoagulants

In some embodiments of the insulin formulation described herein, the insulin adjunctive excipients further comprise one or more anti-thrombosis agents. In further embodiments, the anti-thrombosis agents comprise heparin.

Cell Self Markers

In some embodiments of the insulin formulation described herein, the insulin adjunctive excipients further comprise one or more cell self markers. In further embodiments, the cell self marker comprises or is CD47, a specific fragment of CD47, a specific epitope of CD47, or an analog thereof, or combinations thereof. CD47 is a ubiquitously expressed protein in all human cells, which function as a marker for identifying the cells as "self" to the innate immune system. The identification of CD47, a transmembrane protein that serves as a universal molecular 'marker-of-self', has led to its utilization in the growing development of bio-inspired, immune-evasive devices. Capable of inhibiting phagocytosis and conferring anti-inflammatory properties through interactions with signal regulatory protein alpha (SIRPα) expressed by macrophages, CD47 and its analogs have been found to contribute to the in vivo survival of red blood cells (RBCs), cancer cells, and viruses. In some embodiments, the cell self marker comprises or is a major histocompatibility complex (MHC) class I molecule, a specific fragment of a MHC class I molecule, or a specific epitope of MHC class I molecule, or combinations thereof. a nucleated cells express MHC class I molecules. It has been observed that self-cells are protected from natural killer (NK) cells because of their expression of MHC class I molecules that are recognized by the inhibitory receptors at the surface of NK cells, thus keeping NK cells non-responsive to cells expressing MHC class I molecules. In contrast, infected, or transformed cells that do not express sufficient levels of host MHC class I molecules for effective engagement of inhibitory receptors, are recognized by NK cells as non-self, and are killed.

In some embodiments of the insulin formulation described herein, the insulin is separate from the one or more the insulin adjunctive excipients described herein. For example, insulin is in a chamber or reservoir that is separated from either the insulin dissolution agent or the hyaluronidase in the formulation. In further embodiments, insulin is separated from both the insulin dissolution agents and the hyaluronidase in the formulation. In still further embodiments, insulin is separated from all the insulin adjunctive excipients described herein. In other embodiments, the insulin is mixed with the one or more the insulin adjunctive excipients described herein. For example, insulin is mixed with either insulin dissolution agent or the hyaluronidase in the formulation. In further embodiments, insulin is mixed with both the insulin dissolution agents and the hyaluronidase in the formulation. In still further embodiments, insulin is mixed with all the insulin adjunctive excipients described herein. As used herein, the term "insulin formulation" should be construed to include various combinations: insulin may either be in a separate composition from one or more of the insulin adjunctive excipients described herein; or the insulin may be in the same or a single composition as one or more insulin adjunctive excipients described herein.

In any embodiments of the insulin formulation described herein, the insulin may comprise a slow acting insulin. In other embodiments, the insulin comprises a fast acting insulin. In further embodiments, the insulin is a human insulin. In further embodiments, the insulin includes but not limited to insulin Lispro (Humalog®), insulin Aspart (Novolog®, Novorapid®) and insulin Glulisine (Apidra®), and combinations, co-formulations thereof. In any embodiments of the insulin formulation described herein, the insulin may be in an aqueous solution. In further embodiments, the insulin has a concentration of at least 100 U/mL, at least 150 U/mL, at least 200 U/mL, at least 250 U/ml, or at least 300 U/ml. In any embodiments, the insulin may have a Tmax of less than 20 minutes, less than 15 minutes, or less than 10 minutes when measured at the human physiological temperature.

Embodiments of the insulin formulation described herein exhibits greater hyaluronidase activity than a formulation or composition having the same amount or number of hyaluronidase(s) but without one or more the insulin dissolution agents (e.g. citric acid, salts or substituted citrate derivatives described herein), while maintaining a near neutral pH. The insulin formulation described herein allows for rapid dissociation of hexameric oligomers to monomeric form even at high concentrations of insulin (e.g., above U-100), compared similar concentration of insulin with higher pH known in the art. The insulin in the insulin formulation described herein remains ultra-fast acting (e.g., peak time or Tmax less than 20 or 15 minutes). Another major benefit of the insulin formulation described herein is less skin irritation after injection, which is resulted from the improved PK/PD profile and physiological pH environment.

Furthermore, the insulin formulation described herein may also improve the required hyaluronidase loading due to increased enzymatic activity as compared to a composition without one or more the insulin dissolution agents. For example, the number of active units of insulin is typically decreased from U-100 to U-85 at least partially resulted from the addition of hyaluronidase simply due to volume displacement. Typically, high concentration insulin formulations have a reduced pH to maintain stability of the insulin. As a result, the displacement situation is worsened in a low pH generic insulin U-200 formulation when the insulin is mixed with hyaluronidase, as hyaluronidase is more active in near neutral pH. Without being bound by a particular theory, one may speculate that even more hyaluronidase to be required to achieve the same effect of hyaluron clearance because of hyaluronidase's reduced activity in a low pH environment. Because hyaluronidase is more active in near neutral pH in the insulin formulation described herein, it is expected that less enzyme loading will be required, even at high insulin concentrations. In some embodiments, the hyaluronidase loading in the insulin formulation described herein is decreased by at least 1%, 2%, 5%, 10%, 15%, 20%, 25%, 30%, 35%, 40%, 45% or 50% as compared to a commercial insulin formulation with the same insulin concentration.

In any embodiments of the insulin formulation described herein, the insulin formulation described herein has a insulin concentration of about 10 U/mL, about 20 U/mL, about 30 U/mL, about 40 U/mL, about 50 U/mL, about 60 U/mL, about 70 U/mL, about 80 U/mL, about 90 U/mL, about 100 U/mL, about 125 U/mL, about 150 U/mL, about 175 U/mL, about 200 U/mL, about 225 U/mL, about 250 U/mL, about 275 U/mL, about 300 U/mL, about 325 U/mL, about 350 U/mL, about 375 U/mL, about 400 U/mL, about 425 U/mL, about 450 U/mL, about 475 U/mL, or about 500 U/mL, or a range defined by any two of the preceding values, after the insulin is mixed with one or more adjunctive excipients described herein. In further embodiments, the insulin formulation described herein is at least 100 U/mL, about 125 U/mL, about 150 U/mL, about 175 U/mL, about 200 U/mL, about 225 U/mL, about 250 U/mL, about 275 U/mL, or about 300 U/ml. In further embodiments, the pH of the insulin formulation is near neutral pH, for example, about 6.5, 6.6, 6.7, 6.8, 6.9, 7.0, 7.1, 7.2, 7.3, 7.4 or 7.5, or a range defined by any two of the preceding values. In further embodiments, the insulin formulation described herein may comprise insulin mixed with the adjunctive excipients described herein in a first reservoir and the one or more hyaluronidases is in a second reservoir or component. The hyaluronidase may be alone in the second reservoir or in combination with one or more adjunctive excipients described herein.

In any embodiments of the insulin formulation described herein, the insulin formulation may be used in an insulin infusion device. In further embodiments, the insulin formulation may be used in conjunction with a continuous glucose monitoring device.

Insulin Infusion Devices

Some aspects of the present disclosure relate to a device for administering a insulin formulation described herein. In some embodiments, the insulin infusion device comprises at least one reservoir, containing the insulin formulation described herein. In further embodiments, the insulin infusion device comprises: a first reservoir comprising an effective amount of insulin, wherein the insulin has a pH between about 6.8 and about 7.4; and a second reservoir comprising one or more insulin adjunctive excipients, wherein the insulin adjunctive excipients comprise at least one hyaluronidase.

In some embodiments of the insulin infusion device described herein, the insulin adjunctive excipients in the first or second reservoir may further comprise one or more insulin dissolution agents, anti-platelet agents, anti-thrombosis agents, cell self markers, glucagon, glucagon activating agents, insulin inhibiting agents, or combination thereof. In some such embodiments, one or both the first or the second reservoir further comprises one or more insulin dissolution agents described herein. In further embodiments, the second reservoir further comprises one or more insulin dissolution agents described herein. In further embodiments, the insulin dissolution agents comprise citric acid, a salt, or a substituted derivative thereof. In some embodiments, the insulin in the first reservoir is a fast-acting insulin. In some embodiments, the insulin in the first reservoir is a slow acting insulin. In other embodiments, the insulin in the first reservoir is in a hexameric form. In some embodiments, one or both of the first reservoir and the second reservoir further comprises one or more anti-platelet agents, one or more anti-thrombosis agents, or one or more cell self markers, or combination thereof. In further embodiments, the second reservoir further comprises one or more anti-platelet agents, one or more anti-thrombosis agents, or one or more cell self markers, or combination thereof.

In some embodiments of the insulin infusion device described herein, the device further comprises an administration or delivery mechanism configured to deliver the insulin from the first reservoir to a subject. In further embodiments, the administration mechanism comprises a cannula or a syringe. In one embodiment, the administration mechanism comprises a cannula. In further embodiments, the administration mechanism is coated with one or more anti-platelet agents, one or more anti-thrombosis agents, or one or more cell self markers, or combination thereof. Hyaluronidases in the second reservoir help to breakdown fibrous tissue formed around insulin administration mechanism (e.g., cannula) as a response to the body recognizing the cannula as "non-self" and mounting a response. As an alternatively and/or complimentary approach, the insulin administration or delivery mechanism may be modified to identify itself as "self" to prevent thrombosis and human innate immunity response mechanism (e.g., macrophages, platelets, mast cells etc.) by using more anti-platelet agents (e.g., NO or NO donor compound), one or more anti-thrombosis agents or anticoagulants (e.g., heparin), or one or more cell self markers (e.g., CD47 or MHC class I compound) as described herein, or combinations thereof. In some further embodiments, the administration mechanism further comprises one or more hyaluronidases. In some such embodiments, the hyaluronidase in the administration mechanism is configured to be delivered to the subject prior to the administration of the insulin. For example, the small volume of hyaluronidase needed to prepare the tissue for action can be housed in a cannula or syringe (ahead of the insulin infusion). This configuration may provide two benefits: the hyaluronidase remains unaffected by insulin or other adjunctive excipients, which may make co-formulation difficult; and the natural order of operation occurs: first the hyaluronidase treats the tissue to improve kinetics and second the insulin enters the readied tissue. This could beneficially improve the time of use of an infusion pump beyond 3 days. In some embodiments, the insulin administering device described herein may provide an infusion of insulin up to 7 days or 14 days (for example, 4 days, 5 days, 6 days, 7 days, 8 days, 9 days, 10 days, 11 days, 12 days, 13 days, or 14 days).

In some embodiments of the insulin infusion device described herein, the content in each of the first reservoir and the second reservoir may be administered separately and independently. For example, each of the compartment comprising the first or the second reservoir is a closed loop system. In a first aspect, the insulin in the first reservoir is used alone (without any adjunctive excipients described herein). When insulin is administered alone, it acts more slowly to respond to system states that require a slower response. In some instances, a person can also have unique features that result in personally slower metabolism kinetics related to their gut biome or genetics. In other cases, food intake containing large food particles, fibrous food, solid food, and/or oligo/polysaccharides (carbohydrates) that metabolizes slowly and has a prolonged food response does not necessarily require a very fast acting insulin. Using slow acting insulin in these situations can create a safer insulin response. In a second aspect, the hyaluronidase in the second reservoir may be dispensed alone in order to breakdown a fibrous blockage of the administration mechanism (e.g. cannula).

In other embodiments of the insulin infusion device described herein, the content in each of the first reservoir and the second reservoir may be administered simultaneously or sequentially. In a third aspect, insulin in the first reservoir can be infused at the same time or in a duty cycle with hyaluronidase, insulin dissolution agents (e.g., citric acid, salts thereof, or substituted citrate derivatives described herein) or other enzymes or adjunctive excipients that are in the second reservoir. This administration method may increase the insulin PK/PD from standard or fast acting insulin to ultra-fast acting insulin. This will be very advantageous in situations a quick insulin response is needed. For example, in certain subject with unique features that result in faster food metabolism related to their gut biome or genetics. It will also be helpful when a subject has food intake including a monomeric sugary liquid (monosaccharides such as glucose, fructose, galactose, or disaccharides such as sucrose, lactose, maltose) or other type of food that can be easily metabolized and resulting quick increase of the blood glucose level. The infusion/dispensing rates of the insulin and the adjunctive excipients may be modulated to obtain a continuous range of PK/PD response.

In further embodiments of the insulin infusion device described herein, the second reservoir may further comprise glucagon or a glucagon activating agent. Glucagon is a peptide hormone, produced by alpha cells of the pancreas. Contrary to the function of insulin, it is released to stop blood sugar levels dropping too low (hypoglycemia). A glucagon activating agent is an enzyme or a compound that can stimulate the production and secretion of glucagon (e.g., epinephrine (via $\beta 2$, $\alpha 2$, and $\alpha 1$ adrenergic receptors), arginine, alanine (often from muscle-derived pyruvate/glutamate transamination), acetylcholine, cholecystokinin, or gastric inhibitory polypeptides). In such embodiments, a glucagon activating agent (a compound) in the second reservoir to activate the glucagon may be used to increase the responsiveness of a closed loop system even further. This may also be advantageously used in the three scenarios described herein. In a fourth aspect, the addition of the glucagon activating agent in the second reservoir, (or from a third reservoir by itself) would be helpful when a subject has hypoglycemia. This could also be used in conjunction with a control system that has an additional stimulus as input to the system. The addition of glucagon or a glucagon activating agent may also be used to inhibit or antagonize the insulin that has been administered.

In any embodiments of the insulin infusion device described herein, the insulin may comprise a slow acting insulin. In other embodiments, the insulin comprises a fast acting insulin. In further embodiments, the insulin is a human insulin. In further embodiments, the insulin includes but not limited to insulin Lispro (Humalog®), insulin Aspart (Novolog®, Novorapid®) and insulin Glulisine (Apidra®), and combinations, co-formulations thereof. In any embodiments of the insulin formulation described herein, the insulin may be in an aqueous solution. In further embodiments, the insulin in the first reservoir has a concentration of at least about 100 U/mL, at least about 125 U/mL, at least 150 U/mL, at least about 175 U/mL, at least about 200 U/mL, at least about 225 U/mL, at least about 250 U/mL, at least about 275 U/mL, or at least about 300 U/mL. In any embodiments, the insulin may have a Tmax of less than about 30 minutes, 25 minutes, 20 minutes, 15 minutes, 10 minutes, or 5 minutes when measured at the human physiological temperature.

Insulin Infusion Systems

Additional aspects of the present disclosure relate to a system for administering insulin. In some configurations, the system comprising:
 a device for administering insulin, the device comprises:
  a first reservoir comprising an effective amount of insulin with a pH between about 6.8 and about 7.4; and
  a second reservoir comprising one or more insulin adjunctive excipients, wherein the insulin adjunctive excipients comprise at least one hyaluronidase as described herein;
 an insulin pump configured to administer contents from the device to a subject; and
 one or more hardware processors in communication with the insulin pump.

In some embodiments of the configurations, the one or more hardware processors is configured to: determine a desired insulin response speed; determine, based on the desired insulin response speed, an infusion or insulin alone or an infusion of a combination of insulin and one or more insulin adjunctive excipients; and administer, using the insulin pump, the determined combination. In some embodiments, the insulin adjunctive excipients comprise a hyaluronidases, insulin dissolution agents, anti-platelet agents, anti-thrombosis agents, cell self markers, glucagon, glucagon activating agents, insulin inhibiting agents, or combinations thereof, as described herein. In further embodiments, the device described herein comprises a third reservoir comprising glucagon or a glucagon activating agent.

In some embodiments, the insulin pump administers insulin in the first reservoir by itself. In some embodiments, the insulin pump administers the hyaluronidase in the second reservoir by itself. In some other embodiments, the insulin pump administers the insulin and the hyaluronidase simultaneously or consecutively (e.g., hyaluronidase is administered first and immediately followed by insulin). In still other embodiments, the insulin pump is administering glucagon from the second or third reservoir when the software detects low blood glucose level in a subject. In still other embodiments, glucagon is administered simultaneously or consecutively with insulin when the system detects the blood glucose level is dropping too fast after insulin administration.

Hyaluronidase Adsorption

In any embodiments of the device and system described herein, hyaluronidase can also be used as a surface treatment to either cannulas, or a continuous glucose monitor (CGM) protectant coating as a final layer component. Hyaluronidase may be adsorbed onto the surface of a cannula or CGM protectant as a coating that can be dispersed once in vivo. Depending on the affinity of binding to its base material the desorption can be from hours to days. Adsorption should be considered as another method of administration that helps prevent the need of having another reservoir for infusion.

It is also worth noting, especially for diffusion control of the CGM protectant layer, a bound hyaluronidase through amide crosslinking may prevent formation of the immediate nanometer-scale encapsulation layer around a CGM. This may advantageously reduce the noise due to drift over a 7-14 period of a CGM sensor.

Additional non-limiting embodiments of the insulin infusion device and systems are described in details below.

A. Control System Components

Figure 1B:
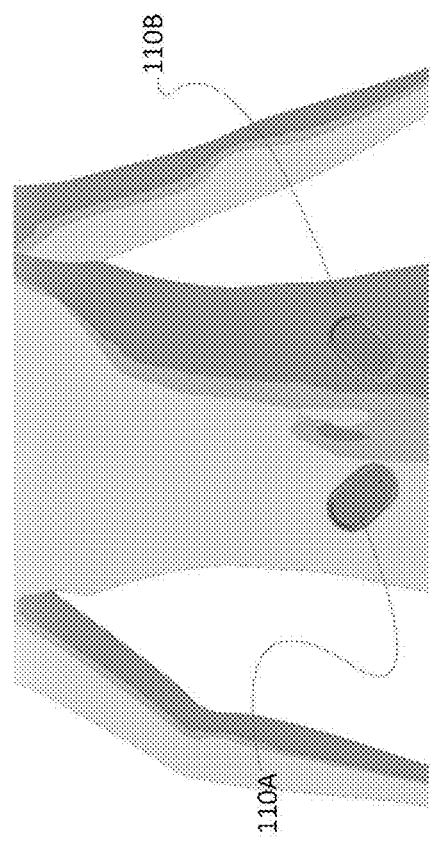
Figure 1C:
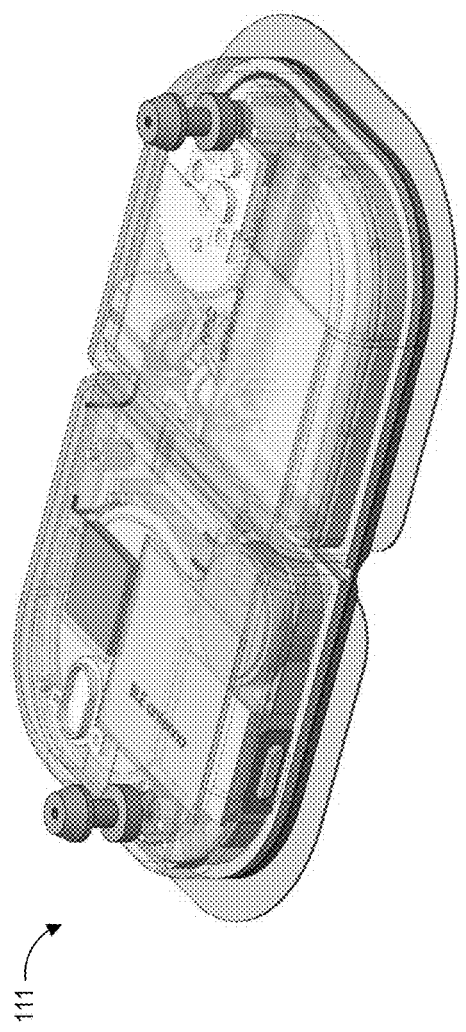

FIGS. 1A-1C illustrates an example closed loop environment 100 in which the administration of an insulin formulation described herein may occur. For example, a closed loop environment 100 may include a user 101, one or more sensor devices 110, one or more user devices 102, a network 104, and a backend system 106.

A user 101 may interact with the one or more sensor devices 110 directly or through one or more user devices 102. The one or more user devices 102 may include a smart device, such as a smart watch, smart phone, tablet, computer, the like or a combination thereof. It should be noted that a user's mobile device, such as a smart phone, may or may not be considered a permanent communication line. In some examples, a user's mobile device, such as a phone, may not be required by the embedded closed loop system to keep the user in tight glycemic control.

In some examples, the one or more user devices 102 may communicate with a sensor device 110 and/or a backend system 106 through a network 104. For example, a user device 102 may receive data from a user 101, such as a time and composition of a user intake of food. The user device 102 may communicate the data, through the network, to the backend system 106. The backend system 106 may then transmit information based on the received data to the user device 102. In some examples, a user device 102 may directly communicate with a sensor device 110 through wires or wirelessly. In some examples, a wireless mode of communication can include, but is not limited to, WiFi, NFC or Bluetooth connection.

In some examples, one or more components of a closed loop system may include at least one sensor device 110. A sensor device 110 may be configured to upload and/or receive data through the user device 102 or the network 104. As illustrated in FIG. 1B, in some examples, one or more hardware components may include two sensor devices 110A, 110B, such as a pair of continuous glucose monitors. In some examples, sensor devices 110 may include a primary sensor device 110A and a secondary sensor device 110B. Advantageously, this may allow for redundancy and staggered active use of glucose sensors so as to allow for at least one glucose sensor 110 to be active and calibrated at any given time during use of the redundant staggered system. In some examples, one or more sensor devices 110A, 110B may include a single sensor device and an insulin pump. In some examples, one or more sensor devices 110A, 110B may include a combined glucose sensor and insulin dosage system 111, such as illustrated in FIG. 1C and as described in U.S. Publication No. 2021/0236729, which is incorporated by reference in its entirety.

In some examples, one or more sensor devices 110A, 110B may include a plurality of reservoirs. For example, each of one or more sensor devices 110A, 110B may include two reservoirs. The first reservoir may be configured to hold insulin. The second reservoir may be configured to hold one or more insulin adjunctive excipients described herein. The one or more sensor devices 110A, 110B may be configured to dispense one or more of the contents of the plurality of reservoirs separately or simultaneously.

B. Separate Reservoirs of Insulin and Excipient(s) and/or Modifier(s)

Figure 2:
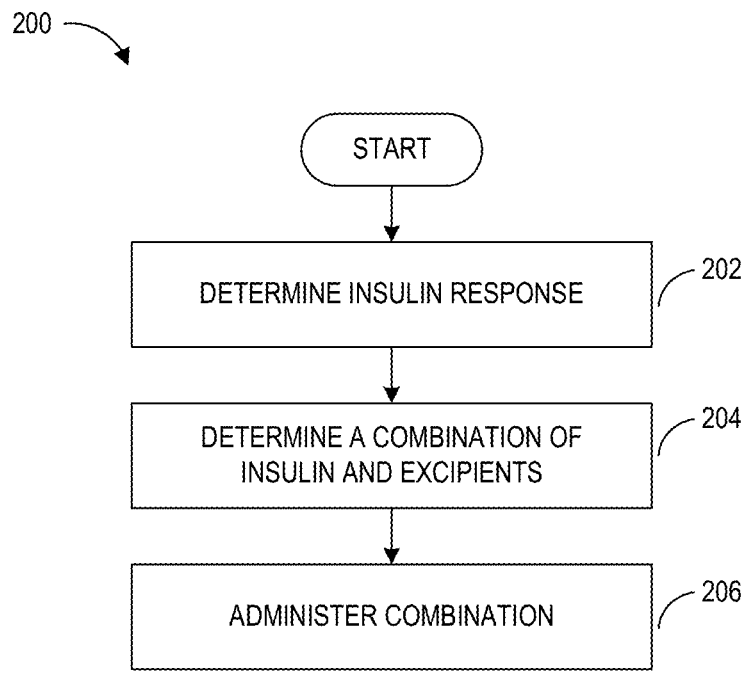
FIG. 2 illustrates an exemplary control process for administering insulin or one or more hyaluronidases.

FIG. 2 illustrates an example control process 200 for administering insulin and one or more insulin adjunctive excipients from separate reservoirs. For example, in a block 202, a hardware processor associated with an insulin administration device may determine a desired insulin response. For example, a desired insulin response may include a slower response because of intake of fibrous foods, such as in the first situation above. In another example, a desired insulin response may include a faster response because of intake of a faster acting meal, such as in the second situation above or as a result of personally faster food kinetics. In another example, a desired insulin response may be associated with a desired breakdown of a fibrous blockage of the cannula, such as in the third situation above. In a block 204, a hardware processor may determine a combination of insulin and excipient to administer. For example, a combination may include insulin alone, a mix of insulin and excipient, or excipient alone. In some examples, excipient may be combined with another chemical compounds, such as glucagon. In a block 206, a hardware processor may administer the combination.

C. Example Disease Management System

Figure 3:
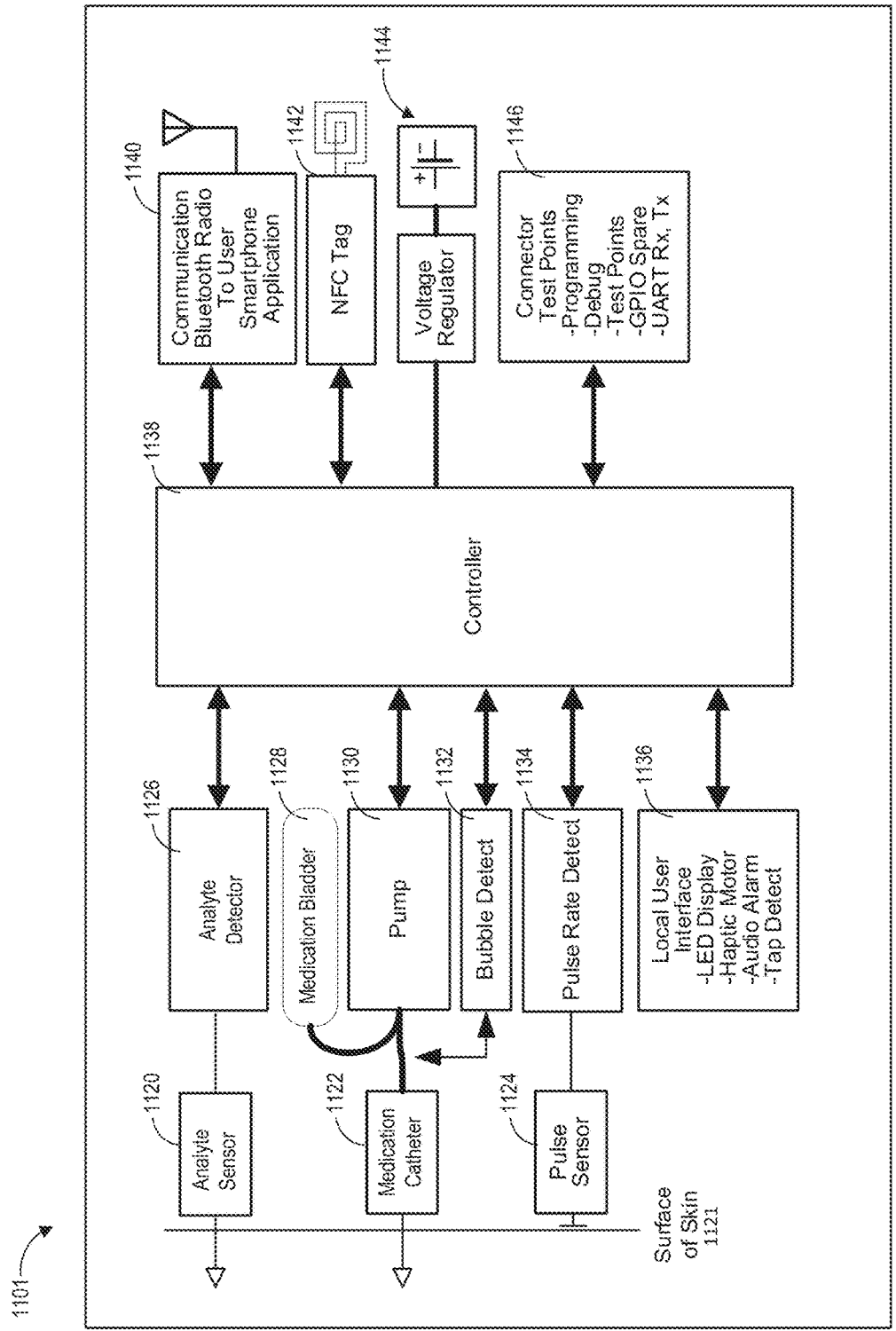
FIG. 3 illustrates an exemplary disease management system that comprises an insulin administering device.

FIG. 3 shows a block diagram of an example disease management system (e.g., prediabetes, Type 1 diabetes, or Type 2 diabetes) 1101, which includes the insulin formulation described herein. In some examples, the disease management system 1101 may be part of a disease management environment, such as described above. A disease management system 1101 may be configured to measure one or more physiological parameters of a patient (such as pulse, skin temperature, or other values), measure one or more analytes present in the blood of a patient (such as glucose, lipids, or other analyte) and administer medication (such as insulin, glucagon, or other medication). In some examples, a disease management system 1101 may be configured to communicate with one or more hardware processors that may be external to the disease management system 1101, such as a cloud based processor or user device. A disease management system 1101 may include an NFC tag to support authentication and pairing with a user device (for example, smart phone or smart watch), Bluetooth communication with additional disease management systems or devices, and Bluetooth communication with a paired user device running an associated control application. To support ease of use and safe interaction with the patient, the system may incorporate user input through a tap-detecting accelerometer and provide feedback via an audio speaker, haptic vibration, and/or optical indicators. The system may operate on battery power and support both shelf-life and reliable operation once applied to the patient. Battery life may be managed through control of several planned levels of sleep and power consumption. To support this reliability, a controller can monitor several system-health parameters, and monitor temperatures of the included medication, and ambient temperature for the life of the device.

As illustrated in FIG. 3, a controller 1138 of the disease management system 1101 may be configured to communicate and control one or more components of the disease management system 1101. The controller 1138 may include one or more hardware processors, such as a printed circuit board (PCB) or the like. The controller 1138 may be configured to communicate with peripheral devices or components to support the accurate measurement of physiological parameters and blood analytes, such as patient pulse, temperature, and blood glucose, using detector electronics. The controller 1138 may subsequently calculate dose or receive a calculated dose value and administer medication, such as a insulin formulation described herein, by actuation of an actuated pump. The controller 1138 may record device activity and transfer the recorded data to non-volatile secure memory space. At the end of the life of a device or system, the controller can be configured to lock operation, and create a data recovery module to permit authenticated access to the recorded data if needed.

A disease management system 1101 may include an analyte sensor 1120. The analyte sensor 1120 may be configured to detect analytes in the patient's blood. For example, an analyte sensor 1120 can include a glucose sensing probe configured to pierce the surface of the skin 1121. In some examples, a disease management system 1101 may include a plurality of analyte sensors 1120 to detect one or more analytes. In some examples, an analyte sensor 1120 may be configured to detect a plurality of analytes. Sensed analytes may include, but are not limited to, glucose, insulin, and other analytes. An analyte sensor 1120 may be configured to communicate with an analyte detector 1126. The analyte detector 1126 may be configured to receive a signal of one or more analyte sensors 1120 in order to measure one or more analytes in the blood of the patient. The analyte detector 1126 may be configured to communicate with the controller 1138. For example, the analyte detector 1126 may be configured to, for example, send analyte values to the controller 1138 and receive control signals from the controller.

A disease management system 1101 may include a medication catheter 1122. The medication catheter 1122 may be configured to administer medication, including, but not limited to insulin, to the patient. The medication catheter 1122 may receive medication from a medication bladder 1128 configured to contain medication to be administered. The medication bladder 1128 may be configured to contain medication for a prolonged period, such as 1 day, 3 days, 6 days, or more. The medication bladder 1128 may be configured to contain certain medication types, such as insulin. In some examples, a disease management system 1101 may include a plurality of medication bladders 1128 for one or more reservoirs of the same or different medications. In some examples, a disease management system 1101 may be configured to mix medications from medication bladders 1128 prior to administration to the patient. A pump 1130 may be configured to cause medication to be administered from the bladder 1128 to the patient through the insulin catheter 1122. A pump 1130 may include, but is not limited to, a pump such as described herein.

A disease management system 1101 may optionally include a physiological sensor 1124. The physiological sensor 1124 may include a pulse rate sensor, temperature sensor, pulse oximeter, the like or a combination thereof. In some examples, a disease management system 1101 may be configured to include a plurality of physiological sensors. The physiological sensor 1124 may be configured to communicate with a physiological detector 1134. The physiological detector 1134 may be configured to receive a signals of the physiological sensor 1124. The physiological detector 1134 may be configured to measure or determine and communicate a physiological value from the signal. The physiological detector 1134 may be configured to communicate with the controller 1138. For example, the physiological detector 1134 may be configured to, for example, send measured physiological values to the controller 1138 and receive control signals from the controller.

A disease management system 1101 may include one or more local user interfacing components 1136. For example, a local user interfacing component 1136 may include, but is not limited to one or more optical displays, haptic motors, audio speakers, and user input detectors. In some examples, an optical display may include an LED light configured to display a plurality of colors. In some examples, an optical display may include a digital display of information associated with the disease management system 1101, including, but not limited to, device status, medication status, patient status, measured analyte or physiological values, the like or a combination thereof. In some examples, a user input detector may include an inertial measurement unit, tap detector, touch display, or other component configured to accept and receive user input. In some examples, audio speakers may be configured to communicate audible alarms related to device status, medication status user status, the like or a combination thereof. A controller 1138 may be configured to communicate with the one or more local interfacing components 1136 by, for example, receiving user input from the one or more user input components or sending control signals to, for example, activate a haptic motor, generate an output to the optical display, generate an audible output, or otherwise control one or more of the local user interfacing components 1136.

A disease management system 1101 may include one or more communication components 1140. A communication component 1140 can include, but is not limited to one or more radios configured to emit Bluetooth, cellular, Wi-Fi, or other wireless signals. In some examples, a communication component 1140 can include a port for a wired connection. Additionally, a disease management system 1101 may include an NFC tag 1142 to facilitate in communicating with one or more hardware processors. The one or more communication components 1140 and NFC tag 1142 may be configured to communicate with the controller 1138 in order to send and/or receive information associated with the disease management system 1101. For example, a controller 1138 may communicate medication information and measured values through the one or more communication components 1140 to an external device. Additionally, the controller 1138 may receive instructions associated with measurement sampling rates, medication delivery, or other information associated with operation of the management system 1101 through the one or more communication components 1140 from one or more external devices.

A disease management system 1101 may include one or more power components 1144. The power components may include, but are not limited to one or more batteries and power management components, such as a voltage regulator. Power from the one or more power components 1144 may be accessed by the controller and/or other components of the disease management system 1101 to operate the disease management system 1101.

A disease management system 1101 may have one or more power and sleep modes to help regulate power usage. For example, a disease management system 1101 may have a sleep mode. The sleep mode may be a very low power mode with minimal functions, such as the RTC (or real time clock) and alarms to wake the system and take a temperature measurement of the system, or the like. In another example, a disease management system 1101 may include a measure temperature mode which may correspond to a low power mode with reduced functions. The measure temperature mode may be triggered by the RTC where the system is configured to take a temperature measurement, save the value, and return the system to a sleep mode. In another example, a disease management system 1101 may include a wake up mode. The wake up mode may be triggered by an NFC device and allow the system to pair with an external device with, for example, Bluetooth. If a pairing event does not occur, the system may return to sleep mode. In another example, a disease management system 1101 may include a pairing mode. The pairing mode may be triggered by an NFC device. When a controlling application is recognized, the system may proceed to pair with the application and set the system to an on condition and communicate to the cloud or other external device to establish initial data movement. In another example, a disease management system 1101 may include a rest mode where the system is configured to enter a lower power mode between measurements. In another example, a disease management system 1101 may include a data acquisition mode where the system is configured to enter a medium power mode where data acquisition takes place. In another example, a disease management system 1101 may include a parameter calculation mode where the system is configured to enter a medium power mode where parameter calculations, such as a blood glucose calculations, are performed and data is communicated to an external device and/or the cloud. In another example, a disease management system 1101 may include a pump mode where the system is configured to enter a higher power mode where the pump draws power to deliver medication to the patient.

A disease management system 1101 may include one or more connector test points 1146. The connecter test points may be configured to aid in programming, debugging, testing or other accessing of the disease management system 1101. In some examples, connector test points 1146 may include, for example, a GPIO spare, UART receiver or transmitter, the like or a combination thereof.

Figure 4:
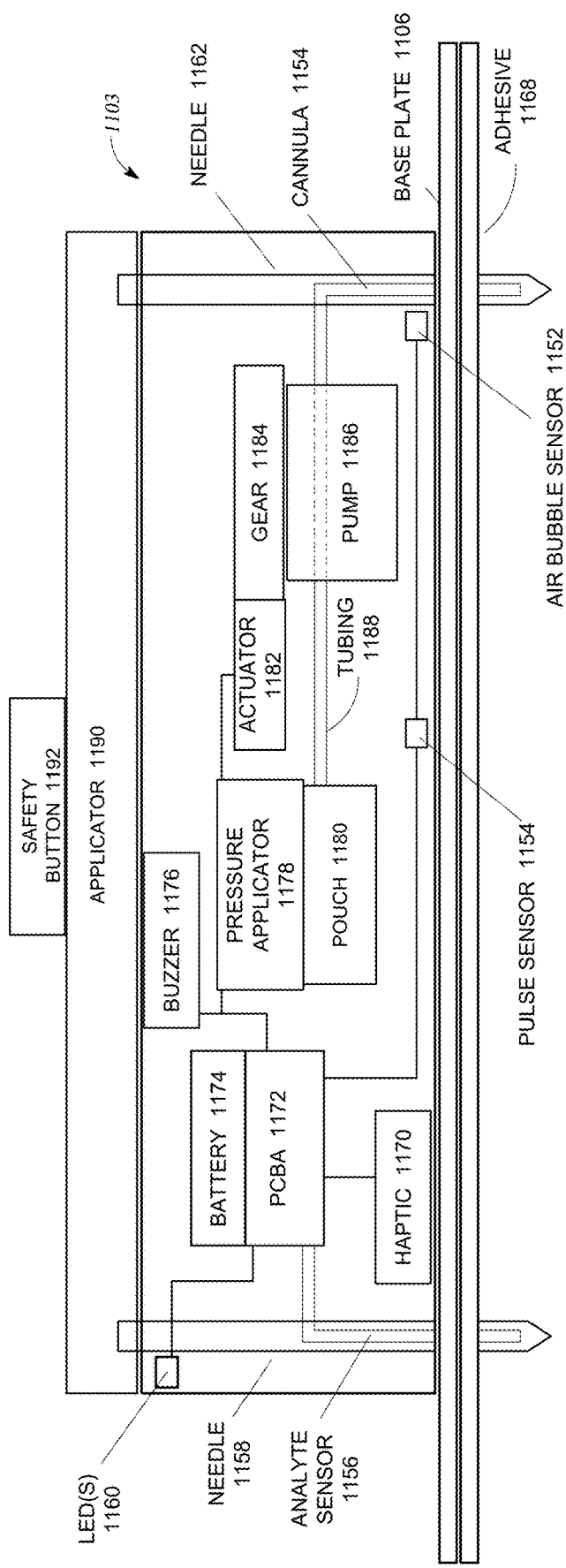
FIG. 4 illustrates an exemplary implementation of a disease management system described herein.

FIG. 4 illustrates an example implementation of a disease management system 1103 and applicator 1190 for applying a disease management system 1103 to a patient. Disease management system 1103 can include any one or more of the features discussed above with respect to the disease management system 1101 in addition to the features described below. In the illustrated example, an applicator 1190 may be configured to mate with the disease management system 1103. In some examples, an applicator 1190 may include a safety button 1192 for release or other interaction with the applicator 1190. In the illustrated example, a disease management system 1103 may include one or more LEDs 1160 that may be configured to output information using one or more of color, frequency, and length of display. In some examples, the disease management system 1103 may include a buzzer 1176, haptic actuator 1170, or other feedback mechanism, such as a speaker to output information to the patient, such as an alarm. In some examples, a disease management system 1103 may include a battery 1174, controller 1172. In some examples, a disease management system 1103 may include aspects of a medication administration system (e.g. an insulin administration system), such as a bladder 1180, a bladder pressure applicator 1178 to provide pressure on the bladder (such as a component of a pump), actuator 1182, pump gears 1184, and a pump 1186. In some examples, a disease management system 1103 may include one or more needles 1158 that may include one or more analyte sensors (such as a glucose sensor) 1156. In some examples, a disease management system 1103 may include one or more needles 1162 that may include one or more cannulas 1164 configured to administer medication to the patient (e.g., an insulin formulation described herein). In some examples, a disease management system 1103 may include an air bubble sensor 1152 configured to detect the presence of air bubbles in the medication prior to delivery to the patient. In some examples, a glucose control system 1103 may include one or more physiological sensors 1154, such as a non-invasive physiological sensor including but not limited to a pulse sensor. In some examples, the disease management system 1103 may include a base plate 1106 and an adhesive layer 1168 below the base plate 1106 to provide adhesion of the disease management system 1103 to the patient's skin. As described below, a housing of the disease management system 1103 may consist of a combination of flexible and rigid material so as to both provide support for the components of the disease management system 1103 and allow conforming, at least in part, of the disease management system 1103 to the skin of the patient.

The adhesive layer 1168 may be configured to provide adhesion for a prolonged period. For example, the adhesive layer 1168 may be configured to adhere the disease management system 1103 to the skin of a patient for a period of 1 day, 3 days, 6 days, or more or fewer days or hours. In some examples, the adhesive layer may be configured to have an adhesive force sufficient to prevent accidental removal or movement of the disease management system 1103 during the intended period of use of the disease management system 1103. In some examples, the adhesive layer 1168 may be a single layer of adhesive across at least a portion of a surface the disease management system 1103 that is configured to interface with the patient. In some examples, the adhesive layer 1168 may include a plurality of adhesive areas on a surface of the disease management system 1103 that is configured to interface with the patient. In some examples, the adhesive layer 1168 may be configured to be breathable, adhere to the patient's skin after wetting by humidity or liquids such as tap water, saltwater, and chlorinated water. A thickness of the adhesive may be, for example, in a range of 0.1 to 0.5 mm or in a range of more or less thickness.

In some examples, a needle 1158, 1162 may be inserted at different depths based on a patient age, weight, or other parameter. For example, a depth of insertion of a medication cannula may be approximately 3 mm for 7 to 12 year olds. In another example, a depth of insertion of a medication cannula may be approximately 4 mm for 13 year olds and older. In another example, a depth of insertion of a medication needle may be approximately 4 to 4.5 mm for 7 to 12 year olds. In another example, a depth of insertion of a medication needle may be approximately 5 to 5.5 mm for 13 year olds and older. In another example, a depth of insertion of an analyte sensor may be approximately 3 mm for 7 to 12 year olds. In another example, a depth of insertion of an analyte sensor may be approximately 4 mm for 13 year olds and older. In another example, a depth of insertion for a needle associated with an analyte sensor may be approximately 4 to 4.5 mm for 7 to 12 year olds. In another example, a depth of insertion for a needle associated with an analyte sensor may be approximately 5 to 5.5 mm for 13 year olds and older. However, other values or ranges for any of the inserted components are also possible.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A system for administering insulin, the system comprising:
   a sensor configured to detect blood glucose concentration of a subject;
   a device for administering insulin, the device comprising
      a first reservoir comprising an effective amount of insulin, wherein the insulin has a pH between about 6.8 and about 7.4; and
      a second reservoir comprising one or more insulin adjunctive excipients, wherein the insulin adjunctive excipients comprise at least one hyaluronidase;
   an insulin pump configured to administer contents from the device to the subject;
   one or more hardware processors in communication with the insulin pump, the one or more hardware processors configured to:
      receive a signal from the sensor indicative of a blood glucose concentration;
      determine, based at least in part on the blood glucose concentration, a desired insulin response speed;
      determine, based on the desired insulin response speed, a first infusion amount of insulin and a second infusion amount of insulin adjunctive excipients; and
      administer, using the insulin pump, the first infusion amount of insulin and the second infusion amount of insulin adjunctive excipients, wherein the volumetric ratio of the first infusion amount and second infusion amount is tunable to achieve a particular pharmacokinetic/pharmacodynamic response from the subject.

2. The system of claim 1, wherein the insulin adjunctive excipients comprise hyaluronidases, insulin dissolution agents, anti-platelet agents, anti-thrombosis agents, cell self markers, glucagon, glucagon activating agents, insulin inhibiting agents, or combination thereof.

3. The system of claim 1, wherein one or both the first or the second reservoir further comprises one or more insulin dissolution agents.

4. The system of claim 3, wherein the insulin dissolution agents comprise citric acid, a salt, or a substituted derivative thereof; oligosaccharides; or combinations thereof.

5. The system of claim 1, wherein the insulin is a slow-acting insulin, a fast-acting insulin, or is in the form of a hexamer, and wherein the insulin in the first reservoir has a concentration of at least 100 U/mL, at least 150 U/mL, or at least 200 U/mL.

6. The system of claim 1, wherein one or both of the first reservoir and the second reservoir further comprises one or more anti-platelet agents, one or more anti-thrombosis agents, or one or more cell self markers, or combination thereof.

7. The system of claim 1, further comprising an administration mechanism configured to deliver the insulin from the first reservoir to a subject.

8. The system of claim 7, wherein the administration mechanism comprises a cannula or a syringe.

9. The system of claim 7, wherein the administration mechanism is coated with one or more anti-platelet agents, one or more anti-thrombosis agents, or one or more cell self markers, or combination thereof.

10. The system of claim 7, wherein the administration mechanism further comprises one or more hyaluronidases.

11. The system of claim 10, wherein the one or more hyaluronidase in the administration mechanism are configured to be delivered to the subject prior to the administration of the insulin.

12. The system of claim 1, wherein the second reservoir further comprises glucagon or a glucagon activating agent.

13. The system of claim 1, wherein the content in each of the first reservoir and the second reservoir are administrable independently or simultaneously.

* * * * *